United States Patent [19]

Voegeli

[11] Patent Number: 4,473,641
[45] Date of Patent: Sep. 25, 1984

[54] METHOD FOR PRODUCING PROTEIN

[76] Inventor: Henry E. Voegeli, Amity Rd., Bethany, Conn. 06525

[21] Appl. No.: 68,616

[22] Filed: Aug. 22, 1979

[51] Int. Cl.$^3$ .............................................. C12P 21/00
[52] U.S. Cl. ...................................... 435/68; 435/248; 435/249; 435/804; 435/874
[58] Field of Search .................. 435/248, 249, 250, 68, 435/804, 874; 210/2, 11, 15

[56] References Cited

U.S. PATENT DOCUMENTS

| | | | |
|---|---|---|---|
| 3,337,413 | 8/1967 | Wegner | 435/248 |
| 3,672,953 | 6/1972 | Coty et al. | 435/248 X |
| 3,816,256 | 6/1974 | Murata et al. | 435/248 X |
| 3,847,803 | 11/1974 | Fisk | 210/11 |
| 3,880,740 | 4/1975 | Mimura et al. | 210/11 |

OTHER PUBLICATIONS

Voegeli et al., "Protein Production by a Mixed Bacterial Culture Using Paracril 1880 and Selected Nitrogen Sources", Cited in Chemical Abstracts, (1978), 184875b.
Nickerson et al., "Microbial Degradation & Transformation of Natural & Synthetic Polymeric Substances", Chemical Abstracts, vol. 87, (1977), Abstract No. 18756g.
Faber et al., "Growth of Microorganisms on Insoluble Polymers: Transformation of Automoile Tires", Chemical Abstracts, vol. 90, (1979), Abstract No. 188254w.
Prokop et al., "Insoluble Substrate and $O_2$ Transport in Hydrocarbon Fermentation", Single Cell Protein, Tannenbaum et al., Editors, MIT Press Publishers, 1975, pp. 127–132.
Rose et al., "The Condensed Chemical Dictionary", Van Nostrand Reinhold Co., 7th Edition, 1970, pp. 824–825.

*Primary Examiner*—R. B. Penland
*Attorney, Agent, or Firm*—Bachman and LaPointe

[57] ABSTRACT

Protein is produced by bacterial degradation of rubber in a nutrient-containing, preferably sterile environment. The resultant protein is particularly useful as an animal feed.

11 Claims, No Drawings

METHOD FOR PRODUCING PROTEIN

BACKGROUND OF THE INVENTION

Inexpensive protein production, as for animal feed, is particularly desirable for a variety of obvious reasons. It is even more desirable to be able to produce the protein in a convenient and simple manner abundant waste products which would otherwise pollute the environment.

For example, discarded rubber tires and buffings produced in recapping operations are abundant and readily available at little or no cost. Attempts have been made to utilize these tires as marine breakwaters, in the formulation of asphalt highways, for improving soil texture, for pillows, and as a fuel source, to cite a few. However, these have not been completely successful.

It is, therefore, a principal object of the present invention to inexpensively and conveniently produce edible protein.

It is a further object of the present invention to produce protein as aforesaid utilizing bacterial degradation of rubber.

Further objects and advantages of the present invention will appear hereinbelow.

SUMMARY OF THE INVENTION

In accordance with the present invention it has now been found that the foregoing objects and advantages may be readily obtained. In accordance with the process of the present invention edible protein is obtained by: providing an aqueous, preferably sterile solution having a pH of 6.0-8.5 maintained at ambient temperatures containing at least 1% of rubber, preferably finely divided, a nitrogen source, preferably urea, in an amount of from 0.1-5% of available nitrogen, and from 0.1-5% of inorganic salts, adding to said solution a hydrocarbon utilizing Pseudomonas bacteria and allowing said bacteria to grow in said solution to protein-containing cells, and harvesting the protein from the cells. The mixture is preferably aerated, as by bubbling air therethrough.

It can be readily seen that the foregoing process represents an inexpensive, convenient and commercially viable method for obtaining edible protein.

Throughout the present specification all percentages are weight percentages.

DETAILED DESCRIPTION

The nutrient solution should preferably be sterile in order to minimize the likelihood of competing reactions. Similarly, as ingredients are added to the solution they should preferably be disinfected and aseptically added.

The rubber is a key component of the mixture. It is a principal object of the present invention to encourage bacteria to grow into cells containing edible protein using the rubber component, preferably as the sole hydrocarbon source. Any rubber may be employed, vulcanized or non-vulcanized, natural or synthetic. Preferred rubbers which can be employed include butadiene-acrylonitrile rubber, styrene-butadiene rubber or natural rubber. Other suitable rubbers include but are not limited to butyl rubber, neoprene rubber, hypalon rubber, nitrile rubber, polyacrylic rubber, butadiene rubber and styrene rubber. These may be readily obtained, for example, from commercial tires or other rubber products as hoses, cable jacketing, etc., or buffings produced in recapping operations. The latter is particularly preferred in view of its small particle size allowing the presentation of a larger surface area to the bacteria. Commercial tires may, if desired, be cut into smaller a size or, less efficiently, may be used in larger size pieces. In order to have a commercially viable process, the solution must contain at least 1% rubber and preferably contains at least 5%. The upper limit is not critical and depends on convenience.

The solution is a nutrient solution and contains from 0.1 to 5% of inorganic salts which provide the following components: alkali metal, alkaline earth metal, sulfur, phosphorus and iron. Halide, preferably chlorine, is also a preferred component. In the preferred embodiment, the salts provide potassium, magnesium, phosphate, sodium, sulfur and chlorine. A particularly preferred solution utilized the following components added to distilled water to provide a sterile, one liter solution:

0.5 g. $KH_2PO_4$
0.5 g. $K_2HPO_4$
0.5 g. $MgSO_4$
4.0 g. NaCl
trace $FeCl_3$

Other salts which can be conventionally employed include but are not limited to: $NaH_2PO_4$; $Na_2HPO_4$; $Ca_3(PO_4)_2$; $Mg_3(PO_4)_2$; $Fe_2(SO_4)_3$; and $MgCl_2$.

A nitrogen source must be added to the solution, generally up to 5% of available nitrogen and as low as 0.1% of available nitrogen. The nitrogen-containing material must have the nitrogen in a form which can be assimilated by and utilized by the organism. Urea has been found to be particularly effective; however, any suitable nitrogen source may be used, as nitrates, especially ammonium nitrate, glutamic acid, milorganite. Nitrates, nitrites and ammonium compounds are particularly suitable.

The solution should be maintained at ambient temperatures, preferably 20°-40° C., and at a pH of from 6.0-8.5.

In the preferred embodiment the sterile medium is prepared by admixing the components and the finely divided rubber component is aseptically added thereto. The rubber should be disinfected, as by allowing to stand for 24 hours in 70% isopropyl alcohol and thereafter allowed to dry.

Any hydrocarbon utilizing bacteria of the Pseudomonas genus can be employed, or mixtures thereof, preferably non-pathogenic. In the experimental procedure a mixture of four bacterial isolates of this genus were employed. Representative Pseudomonas species include but are not limited to the following:

Ps. fluorescens
Ps. putida
Ps. oleovorans
Ps. stutzeri
Ps. testosteroni

The desired bacterial culture is simply added to the sterile solution, preferably in the form of a start-up culture, and the bacteria allowed to grow. If desired, one can even obtain the start-up cultures from samples of tires retrieved from dumping sites, incubated for 5-10 days and subcultured into a fresh media containing alcohol-disinfected tire material. Preferably, the solution is aerated by bubbling air therethrough in order to accelerate the growing process. Harvesting can begin in from 7-14 days, and the process can be run on a continuous basis by simply adding depleted conponents, e.g., periodic additions of salts, nitrogen source and rubber.

The resultant cells are protein-rich and can be simply removed from the solution and the protein separated therefrom by any desired means, as by breaking open the cells. Preferred methods include freezing and thawing, ultrasonics and enzyme lysis of the cell walls.

The present invention and improvements resulting therefrom will be more readily apparent from a consideration of the following illustrative examples.

EXAMPLE I

Five groups of bottles were provided, each containing a sterile solution with 5.0 grams of finely divided butadieneacrylonitrile copolymer and 100 ml. of an aqueous inorganic salt solution. The salt solution was made from the following salts dissolved in a liter of distilled water:

0.5 g. $KH_2PO_4$
0.5 g. $K_2HPO_4$
0.5 g. $MgSO_4$
4.0 g. NaCl
trace $FeCl_3$

One group received 0.5 g. $NH_4NO_3$ as nitrogen source, one received 0.5 g. urea, one received 0.5 g. glutamic acid, one received 0.5 g. milorganite, and the fifth group received no added nitrogen. The pH was pH 6.8.

Each bottle was inoculated with 0.1 ml. of a mixed Pseudomonas bacterial inoculum and incubated at 26° C. for 18 days. A protein analysis of the resulting cells was then made using a trichloroacetic acid protein precipitation procedure. The average protein content for 10 samples is shown in Table I, below. Thus, each of the samples receiving added nitrogen showed protein production higher than the samples with no added nitrogen, although clearly the urea inoculated samples show the most growth.

TABLE I

| SAMPLE NO. | ADDED NITROGEN | MILLIGRAMS PROTEIN PER 100 ml. MEDIUM |
| --- | --- | --- |
| 1. | none | 1.3 |
| 2. | urea | 7.8 |
| 3. | glutamic acid | 4.5 |
| 4. | ammonium nitrate | 3.2 |
| 5. | milorganite | 1.8 |

EXAMPLE II

The procedure of Example I was substantially repeated. Urea was used as the nitrogen source in each case, with 0.375 g. of urea aseptically added per liter of sterile medium. In addition to the butadiene-acrylonitrile copolymer, samples of natural rubber and styrene-butadiene rubbers were tested. Some samples were aerated at a rate of 198 cc. air per minute per flask (each flask contained one liter) by means of a 6 mm. internal diameter glass tube submerged in the bottom of the flask. The air was passed through a sterile cotton filter before entering the flasks. The samples were incubated at 26° C. for 14 days and the results are shown in Table II, below.

TABLE II

| SAMPLE NO. | RUBBER | AERATED | Mg. OF PROTEIN PER LITER |
| --- | --- | --- | --- |
| 6. | butadiene-acrylonite | yes | 368 |
|  |  | no | 75 |
| 7. | natural | yes | 62 |
|  | rubber | no | 25 |
| 8. | styrene-butadiene | yes | 166 |
|  |  | no | 117 |

EXAMPLE III

The procedure of Example II was repeated using natural rubber, styrene-butadiene rubber and tire buffings with aeration. The tire buffings were produced from a commercial automobile tire which is two-ply polyglass plus two-ply polyester belted. The results are shown in Table III, below.

TABLE III

| SAMPLE NO. | RUBBER | Mg. OF PROTEIN PER LITER |
| --- | --- | --- |
| 9. | tire buffings | 83 |
| 10. | natural rubber | 32 |
| 11. | styrene-butadiene | 219 |

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A method for obtaining edible protein which consists essentially of: providing an aqueous, sterile solution at ambient temperature having a pH of from 6.0–8.5 containing solid, finely divided rubber in an amount of at least 1% selected from the group consisting of butadiene-acrylonitrile rubber, styrene-butadiene rubber, natural rubber, butyl rubber, neoprene rubber, hypalon rubber, nitrile rubber, polyacrylic rubber, butadiene rubber, styrene rubber, and mixtures thereof, a nitrogen source in an amount of 0.1–5% of available nitrogen, and from 0.1–5% of inorganic salts; adding hydrocarbon-utilizing Pseudomonas bacteria to said solution, and allowing said bacteria to grow to protein-containing cells wherein said solution is aerated while said bacteria is growing; and harvesting the protein from the cells.

2. A method according to claim 1 wherein the rubber is the only hydrocarbon source.

3. A method according to claim 1 wherein the temperature is maintained at 20°–40° C.

4. A method according to claim 1 wherein said salts provide alkali metal, alkaline earth metal, sulfur, phosphorus and iron.

5. A method according to claim 4 wherein said salts also provide chloride.

6. A method according to claim 5 wherein said salt mixture includes potassium dihydrogen phosphate, potassium monohydrogen phosphate, magnesium sulfate, sodium chloride and ferric chloride.

7. A method according to claim 1 wherein said nitrogen source is selected from the group consisting of urea, glutamic acid, milorganite, and mixtures thereof.

8. A method according to claim 1 wherein the rubber is a butadiene-acrylonitrile rubber.

9. A method according to claim 1 wherein said rubber is a styrene-butadiene rubber.

10. A method according to claim 1 wherein said rubber is a natural rubber.

11. A method according to claim 1 wherein said rubber is disinfected prior to providing said solution.

* * * * *